United States Patent [19]

Murakami et al.

[11] Patent Number: 5,153,329
[45] Date of Patent: Oct. 6, 1992

[54] PROCESS FOR PRODUCING N-ALKYLPYRAZOLES

[75] Inventors: Hiroshi Murakami, Narashino; Susumu Yamamoto, Yachiyo; Yoshihiro Iwasawa; Fumio Suzuki, both of Funabashi; Isao Hashiba, Onoda, all of Japan

[73] Assignee: Nissan Chemical Industries Ltd., Tokyo, Japan

[21] Appl. No.: 678,241

[22] Filed: Apr. 1, 1991

[30] Foreign Application Priority Data

Apr. 3, 1990 [JP] Japan ................................. 2-88491
Apr. 18, 1990 [JP] Japan ................................ 2-102359

[51] Int. Cl.$^5$ ............................................. C07D 231/12
[52] U.S. Cl. ...................................................... 548/373.1
[58] Field of Search ............................................ 548/373

[56] References Cited

U.S. PATENT DOCUMENTS 2,931,814  4/1960  Karmas .

OTHER PUBLICATIONS

*Acta Chemica Scandinavica,* vol. 44, pp. 1050-1057, (1990), "Alkylation, Acylation and Silylation of Azols" M. Begtrup et al.

*Primary Examiner*—Robert W. Ramsuer
*Attorney, Agent, or Firm*—Oblon, Spivak, McClelland, Maier & Neustadt

[57] ABSTRACT

Disclosed herein is a process for producing N-alkylpyrazoles represented by the formula (1), which comprises reacting an alkali metal or an alkali metal-containing base with N-unsubstituted pyrazoles represented by the formula (2), to form an alkali metal salt thereof and, subsequently, reacting the obtained alkali metal salt with an alkylating agent.

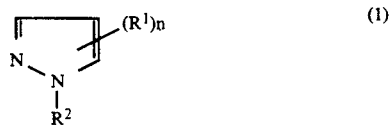

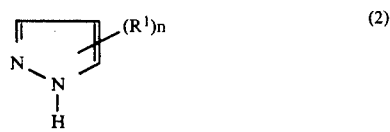

$R^1$: H, $C_1$-$C_4$ alkyl;
$R^2$: $C_1$-$C_4$ alkyl;
n: an integer of 1-3.

10 Claims, No Drawings

PROCESS FOR PRODUCING N-ALKYLPYRAZOLES

BACKGROUND OF THE INVENTION

The present invention relates to a process for producing N-alkyl pyrazoles which are useful as an intermediate for medicines and agricultural chemicals, in particular, as an intermediate for herbicides.

As for the N-alkylation method for pyrazoles, methods to be described hereinafter have been known.

(1) A method of reacting 4-methylpyrazole and dimethyl sulfate in an aqueous 2N solution of sodium hydroxide is disclosed in Justus Liebigs Annalen der Chemie, 625, 55 (1959). However, the yield of 1,4-dimethylpyrazole in this method is as low as 56%.

(2) A method of reacting 3(5)-methylpyrazole and methyl iodide in the presence of sodium methoxide in a methanol solution to obtain 1,3-dimethylpyrazole and 1,5-dimethylpyrazole is disclosed in Chemisch Berichte, 59, 1282 (1926). However, no satisfactory results are obtainable by this method (refer to Comparative Examples 1 and 2 to be described later).

It has strongly be demanded for providing a process for producing N-alkylpyrazoles useful as an intermediate for medicines and agricultural chemicals at a high yield.

As a result of the present inventors' earnest study for satisfying the foregoing demand, it has been found that N-alkylpyrazoles represented by the formula (1) can be obtained at a high yield by reacting an alkali metal or an alkali metal-containing base with N-unsubstituted pyrazoles represented by the formula (2) to form an alkali metal salt thereof and, subsequently, reacting the obtained alkali metal salt of pyrazoles with alkylating agents.

(wherein $R^1$ represents a hydrogen atom or a $C_1$-$C_4$ alkyl group, $R^2$ represents a $C_1$-$C_4$ alkyl group and n represents an integer of 1 to 3).

The present invention has been attained on the basis of the above-mentioned finding.

SUMMARY OF THE INVENTION

In an aspect of the present invention, there is provided a process for producing N-alkylpyrazoles represented by the formula (1), which comprises reacting an alkali metal or an alkali metal-containing base with N-unsubstituted pyrazoles represented by the formula (2) to form an alkali metal salt thereof and, subsequently, reacting the obtained alkali metal salt of pyrazoles with on alkylating agent.

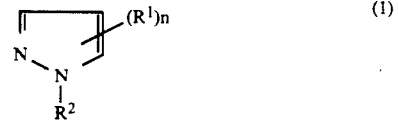

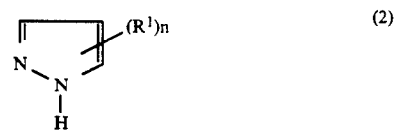

(wherein $R^1$ represents a hydrogen atom or a $C_1$-$C_4$ alkyl group and $R^2$ represents a $C_1$-$C_4$ alkyl group and n represents an integer of 1 to 3).

DETAILED DESCRIPTION OF THE INVENTION

As the alkali metal or the alkali metal-containing base, there can be used an inorganic base such as sodium hydride, potassium hydride, lithium hydride, sodium metal, metal potassium, metal lithium metal, lithium aluminum hydride, sodium borohydride, lithium borohydride, butyl lithium, lithium diisopropylamide, sodium hydroxide, potassium hydroxide, lithium hydroxide, sodium carbonate and potassium carbonate, and an organic base such as sodium methoxide, sodium ethoxide, potassium methoxide, potassium ethoxide, potassium t-butoxide, trimethylamine, triethylamine and pyridine.

A preferred amount of the alkali metal or alkali metal-containing base used is within a range usually from 0.7 to 5.0 mol, preferably 1.0 to 2.0 mol based on one mol of N-unsubstituted pyrazoles. The reaction temperature is from $-10°$ to $200°$ C. and the reaction time is from 0.5 to 30 hours.

As the alkylating agent, there can be mentioned alkyl halide such as methyl chloride, methyl bromide, methyl iodide, ethyl chloride, ethyl bromide, ethyl iodide, propyl chloride, propyl bromide, propyl iodide, isopropyl chloride, isopropyl bromide, isopropyl iodide and butyl bromide, and dimethyl sulfate and diethyl sulfate.

A preferred amount of the alkylating agent used is within a range usually from 0.4 to 10.0 mol, preferably 0.5 to 5.0 mol based on one mol of N-unsubstituted pyrazoles. The reaction temperature is usually within range from $-10°$ to $200°$ C. and the reaction time is from 0.5 to 30 hours.

The reaction of the present invention can be conducted without solvent but a solvent may be used. As the solvent, there can be mentioned aliphatic hydrocarbons such as hexane and heptane; halogenated hydrocarbons such as methylene chloride and 1,1,1-trichloroethane; aromatic hydrocarbons such as benzene, toluene and xylene; halogen-substituted aromatic hydrocarbons such as chlorobenzene, dichlorobenzene and 3,4-dichlorotoluene; alkoxy-substituted aromatic hydrocarbons such as anisole and 1,2-dimethoxybenzene; ethers such as diethyl ether, dipropyl ether, methyl tertiary butyl ether, ethylene glycol dibutyl ether, diethylene glycol dibutyl ether, tetrahydrofuran and dioxane; and aprotic polar solvents such as N,N'-dimethylformamide and acetonitrile. In addition, for forming the alkali metal salt of pyrazoles, alchols such as methanol, ethanol, butanol and amylalcohol can also be used. Two or more of the above-mentioned solvents can also be used as mixture or dispersion.

The reaction of the present invention can be applied either in an atmospheric pressure or under pressure.

In particular, an alkali metal salt of N-unsubstituted pyrazoles can be produced industrially at a good yield by the following methods.

The first method is a process for producing an alkali metal salt of N-unsubstituted pyrazoles by reacting N-unsubstituted pyrazoles with sodium metal, or potassium metal, etc. The reaction may be proceeded without solvent but the inert solvent as described above may also be used. Further, metal sodium, metal potassium or the like may be used as such in the state of solid but it is preferred to react them in a molten state.

Alternatively, the second method is a process for producing an alkali metal salt of pyrazoles at a good efficiency by reacting N-unsubstituted pyrazoles with sodium methoxide, sodium ethoxide, potassium methoxide, potassium ethoxide, potassium t-butoxide, sodium hydroxide, potassium hydroxide, lithium hydroxide, etc. while distilling off alcohol or water.

Generally, a strongly acidic N-unsubstituted pyrazoles having a strong electron attracting group such as a carboxylic acid ester group or a nitro group as a substituent can easily form a salt with a base, but weakly acidic N-unsubstituted pyrazoles as N-unsubstituted alkyl pyrazole according to the present invention hardly form a salt. For instance, reaction of an alkoxide such as sodium methoxide with N-unsubstituted pyrazoles in an alcohol solvent followed by a treatment with the alkylating agent described above can provide no satisfactory results (refer to Comparative Examples 1 and 2). This is considered to be attributable to that a sodium salt of pyrazoles can not be formed efficiently due to the following equilibrium reaction.

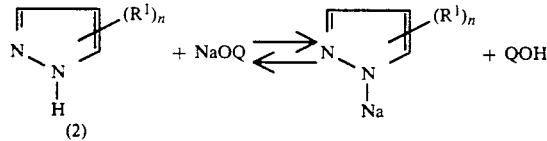

(wherein $R^1$ represents a hydrogen atom or a $C_1-C_4$ alkyl group and Q represents a hydrogen atom or methyl group).

In view of the above, an alkali metal salt of methyl pyrazoles can be formed at a good efficiency by distilling off alcohol or water out of the reaction system, thereby shifting the above-mentioned equilibrium reaction rightward. The reaction can be conducted also in the coexistence of an insert solvent.

Referring to embodiments for practicing the present invention, the first method is a process for obtaining N-alkylpyrazoles represented by the formula (1) by reacting N-unsubstituted pyrazoles with an alkali metal at 60° to 190° C. for 0.5 to 5.0 hours, thereby obtaining an alkali metal salt of pyrazoles and, subsequently, reacting the obtaining alkali metal salt of pyrazoles with an alkylating agent at 20° to 150° C. for 1.0 to 20 hours.

The second method is a process for obtaining N-alkylpyrazoles represented by the formula (1) by reacting N-unsubstituted pyrazoles with alkoxides or alkali hydroxides while distilling off alcohol or water to form an alkali metal salt of pyrazoles and, subsequently, reacting the obtained alkali metal salt of pyrazoles with an alkylating agent at 20° to 150° C. for 1.0 to 20 hours.

After finishing the reaction, inorganic materials in the reaction product are removed by filtration or adding water to the reaction mixture and extracting the reaction product with an organic solvent and, subsequently, N-alkylpyrazoles represented by the formula (1) can be obtained by means of distillation or the like.

In accordance with the present invention, N-alkylation for N-unsubstituted pyrazoles can be conducted also within an industrial scale and N-alkylpyrazoles represented by the formula (1) can be obtained at a high yield.

In particular, the present invention is effective as a process for producing 1,4-dimethylpyrazole. 1,4-dimethylpyrazole useful as an intermediate for herbicides [refer to Japanese Patent Application Laid-Open (KOKAI) 60-208977 (Corresponding to U.S. Pat. Nos. 4,668,277 and 4,689,417)] used in corn farms (Japanese Patent Application Laid-Open (KOKAI) 2-191259).

As shown in Comparative Examples 1 and 2 described later, the conversion ratio is low and the yield of N-alkylpyrazoles is lower than 50% in the conventional method, whereas in the present invention the conversion ratio is high, for example, not lower than 80% and the yield of N-alkylpyrazoles is not lower than 80%, and depending on the reaction conditions, it can be obtained at a high yield of not lower than 95%.

EXAMPLE

The present invention will be explained referring to examples but the present invention is not restricted to them.

EXAMPLE 1

In 5 g of dry toluene, 0.25 g (0.0109 mol) of metal sodium was put to a molten state at a temperature of 100° to 105° C., to which 1.0 g (87.8% purity, 0.0107 mol) of 4-methylpyrazole was added under stirring for 10 min. After the dropping was over, it was stirred for further 45 min at 100° to 105° C. and then the temperature was returned to a room temperature. After adding 6 ml of tetrahydrofuran, 1.60 g (0.0113 mol) of methyl iodide was dropped for 5 min and, after stirring for 3 hours, inorganic matters were separated by filtration. When the liquid filtrate was analyzed on liquid chromatography, 0.89 g of 1,4-dimethylpyrazole was contained therein. The conversion ratio was 88% and the yield was 87% based on 4-methylpyrazole.

EXAMPLE 2

0.25 g (0.0109 mol) of metal sodium was put to a molten state in a reflux of 5 g of dry dioxane, to which 1.0 g (87.8% purity, 0.0107 mol) of 4-methylpyrazole was dropped for 10 min stirred for 5 hours in a refluxing state and then the temperature was returned to a room temperature. After dropping 1.60 g (0.0113 mol) of methyl iodide for 5 min and stirring for 2 hours, inorganic matters were separated by filtration. When the liquid filtrate was analyzed on liquid chromatography, 0.91 g of 1,4-dimethylpyrazole was contained therein. The conversion ratio was 91% and the yield was 88% based on 4-methylpyrazole.

EXAMPLE 3

0.27 g (0.0117 mol) of metal sodium was added to 1.7 g of dry methanol at a room temperature and solved under stirring to prepare sodium methoxide. After adding 5 g of heptane, 1.0 g (87.8% purity, 0.0107 mol) of 4-methylpyrazole was dropped for 5 min under stirring. After stirring at a room temperature for 30 min, the temperature was elevated to 80° C. and methanol was distilled off for one hour and, further, methanol was distilled off at 90° C. for one hour. After returning the temperature to a room temperature and adding 5 g of tetrahydrofuran, 1.67 g (0.0118 mol) of methyl iodide was dropped for 5 min. After stirring for 4 hours, inorganic matters were separated by filtration. When the liquid filtrate was analyzed on liquid chromatography, 0.96 g of 1,4-dimethylpyrazole was contained therein. The yield was 94% based on 4-methylpyrazole.

EXAMPLE 4

0.27 g (0.0117 mol) of metal sodium was put to a molten state in a reflux of 5 g of dry dioxane, to which 1.0 g (87.8% purity, 0.0107 mol) of 4-methylpyrazole was dropped for 2 min under stirring. After the dropping was over, they were further stirred for 4 hours and 20 min in a refluxing state, and then the temperature was returned to 40° C. 6.48 g (0.1284 mol) of methyl chloride was blown at 40° C. for 2.5 hours and at 50° C. for 2 hours, and thereafter, inorganic matters were separated by filtration. When the liquid filtrate was analyzed on liquid chromatography, 1.02 g of 1,4-dimethylpyrazole was contained therein. The yield was 99% based on 4-methylpyrazole.

EXAMPLE 5

0.51 g (0.0119 mol) of 93% sodium hydroxide was added to 2.1 g of dry methanol and dissolved at 50° C. After adding 5 g of heptane, 1.0 g (87.8% purity, 0.0107 mol) of 4-methylpyrazole was dropped under stirring for 5 min. After stirring for 30 min, the temperature was elevated and methanol was distilled off at 75° to 90° C. for 2.0 hours. Subsequently, the temperature was returned to a room temperature, 5 g of tetrahydrofuran was added and 1.67 g (0.0118 mol) of methyl iodide was dropped for 5 min. After stirring for 5 hours, inorganic matter were separated by filtration. When the liquid filtrate was analyzed on liquid chromatography, 1.0 g of 1,4-dimethylpyrazole was contained therein, the conversion ratio was 98% and the yield was 97% based on 4-methylpyrazole.

EXAMPLE 6

0.51 g (0.0119 mol) of 93% sodium hydroxide was added to 2.1 g of dry methanol and dissolved at 50° C. After adding 5 g of heptane, 1.0 g (87.8% purity, 0.0107 mol) of 4-methylpyrazole was dropped under stirring for 5 min. After stirring for 30 min, the temperature was elevated and methanol was distilled out at 75° to 95° C. for 2.5 hours. Subsequently, the temperature was returned to a room temperature, 5 g of tetrahydrofuran was added and 1.87 g (0.0168 mol) of 98% ethyl bromide was dropped for 5 min. After stirring for 2 hours, the temperature was elevated to 40° C. and the stirring was continued for 14.5 hours. After separating inorganic matters by filtration, when the liquid filtrate was analyzed on liquid chromatography, 1.04 g of 1-ethyl-4-methylpyrazole was contained therein, the conversion ratio was 94% and the yield was 89% based on 4-methylpyrazole.

EXAMPLE 7

0.57 g (0.0133 mol) of 93% sodium hydroxide was added to 2.3 g of dry methanol and dissolved at 50° C. After adding 5 g of heptane, 1.0 g (99% purity, 0.0121 mol) of 4-methylpyrazole was dropped under stirring for 10 min. After stirring for 30 min, the temperature was elevated and methanol was distilled off at 70° to 90° C. for one hour. Then, the temperature was lowered to 40° C., 5 g of tetrahydrofuran was added and 2.26 g (0.0133 mol) of isopropyl iodide was dropped for 7 min. and stirred for 4 hours. The temperature was further elevated and stirring was applied for 33 hours while refluxing under heating. After separating inorganic matters by filtration, when the liquid filtrate was analyzed on liquid chromatography, 1.13 g of 1-isopropyl-4-methylpyrazole was contained therein. The conversion ratio was 86% and the yield was 83% based on 4-methylpyrazole. Boiling point was 61°–65° C./18 mmHg.

EXAMPLE 8

After adding a solution of 1.08 g (0.0251 mol) of 93% sodium hydroxide dissolved in 6 g of methanol to a liquid mixture containing 2.0 g (93.5% purity, 0.0228 mol) of 4-methylpyrazole and 10 g of chlorobenzene, temperature was elevated and methanol was distilled off at 100° C. of an outer bath. Then, the temperature was lowered and methyl chloride was blown at 50°–55° C. at a rate of 10 ml per one min for 9 hours. After separating inorganic matters by filtration, when the filtrate was analyzed on liquid chromatography, 2.15 g of 1,4-dimethylpyrazole was contained therein, the yield was 98% based on 4-methylpyrazole.

EXAMPLE 9

After adding a solution of 1.08 g (0.0251 mol) of 93% sodium hydroxide dissolved in 6 g of methanol to a liquid mixture containing 2.0 g (93.5% purity, 0.0228 mol) of 4-methylpyrazole and 45 g of methyl tertiary butyl ether, the temperature was elevated and methanol was distilled off at 51°–53° C. by azeotropic boiling with methyl tertiary butyl ether. Then, methyl chloride was blown at 50°–55° C. at a rate of 10 ml per one min for 18 hours. After separating inorganic matters by filtration, when the filtrate was analyzed on liquid chromatograpy, 2.02 g of 1,4-dimethylpyrazole was contained therein. The conversion ratio was 93% and the yield was 92% based on 4-methylpyrazole.

EXAMPLE 10

After adding a solution of 1.08 g (0.0251 mol) of 93% sodium hydroxide dissolved in 5 g of methanol to a liquid mixture containing 2.0 g (93.5% purity, 0.0228 mol) of 4-methylpyrazole and 10 g of 1,2-dimethoxybenzene, temperature was elevated and methanol was distilled off at 100° C. of an outer bath. Then, the temperature was lowered and methyl chloride was blown at 50°–55° C. at a rate of 10 ml per one min for 3.5 hours. After separating inorganic matters by filtration, when the filtrate was analyzed on liquid chromatography, 2.17 g of 1,4-dimethylpyrazole was contained therein. The yield was 99% based on 4-methylpyrazole.

EXAMPLE 11

1.10 g (0.0478 mol) of metal sodium was added to 10 g of dry methanol to prepare sodium methoxide. After adding 20 g of heptane, 4.0 g (0.0488 mol) of 3-methylpyrazole was dropped under stirring for 5 min. After stirring for 30 min, the temperature was elevated and methanol was distilled off at 75°–90° C. for 2.0 hours. Then, the temperature was returned to a room temperature, 20 g of tetrahydrofuran was added and 9.26 g (0.0652 mol) of methyl iodide was dropped for 5 min. After stirring for 2 hours, inorganic matters were separated by filtration. When the liquid filtrate was analyzed on gas chromatography, 4.3 g of a mixture containing 1,3-dimethylpyrazole and 1,5-dimethylpyrazole at 1:1.7 ratio was contained. The conversion ratio was 93% and the yield was 92% based on 3-methylpyrazole.

COMPARATIVE EXAMPLE 1

0.50 g (0.0218 mol) of metal sodium was added at a room temperature to 20 g of dry methanol to prepare sodium methoxide. 2.0 g (84.9% purity, 0.0207 mol) of 4-methylpyrazole was dropped for 5.0 min and stirring was further applied at a room temperature for 30 min. 3.09 g (0.0218 mol) of methyl iodide was dropped for 6 min and after the completion of the dropping, the resultant mixture was stirred for 5.5 hours at a room temperature and for 3 hours at a methyl iodide refluxing temperature. Since the conversion ratio was low, 3.09 g (0.0218 mol) of methyl iodide was further added and stirred for 7 hours at a refluxing temperature. When the reaction solution was analyzed on liquid chromatography, 0.73 g of 4-methylpyrazole and 1.00 g of 1,4-dimethylpyrazole were contained therein. The conversion ratio was 63.5% and the yield was 50% based on the 4-methylpyrazole.

COMPARATIVE EXAMPLE 2

0.55 g (0.0239 mol) of metal sodium was added at a room temperature to 10 g of dry methanol to prepare sodium methoxide. 2.0 g (0.0244 mol) of 3-methylpyrazole was dropped for 5.0 min and the stirring was further continued at a room temperature for 30 min. 4.63 g (0.0326 mol) of methyl iodide was dropped for 20 min and, after completion of the dropping, the resultant mixture was stirred for 5.0 hours at a room temperature. After distilling off methanol, 20 g of water was added to dissolve inorganic matters and the organic matters were extracted with 20 g of diethyl ether. The aqueous layer was extracted for three times with 6 g of diethyl ether, and the obtained extract joined with the above-mentioned organic layer. When the obtained organic layer was analyzed on gas chromatography and liquid chromatography, 1.30 g of 3-methylpyrazole and 0.77 g of a mixture containing 1,3-dimethylpyrazole and 1.5-dimethylpyrazole at 1:1.1 ratio were contained. The conversion ratio was 35% and the yield was 33% based on 3-methylpyrazole.

What is claimed is:

1. A process for producing N-alkylpyrazoles represented by Formula (1):

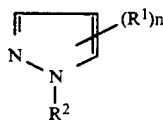

wherein $R^1$ is a $C_1$–$C_4$ alkyl group and $R^2$ is a $C_1$–$C_4$ alkyl group and n is an integer of 1 to 3, which comprises:

reacting an alkali metal or an alkali metal-containing base with an N-substituted pyrazole represented by Formula (2):

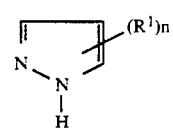

wherein $R^1$ and n are as defined above, thereby forming an alkali metal salt thereof; and, subsequently reacting the alkali metal pyrazole salt obtained with an alkylating agent in a solvent selected from the group consisting of an aliphatic hydrocarbon, an aromatic hydrocarbon, a halogen-substituted aromatic hydrocarbon, an ether and an aprotic polar solvent.

2. The process according to claim 1, wherein said N-unsubstituted pyrazole reactant has Formula (2a):

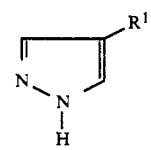

wherein $R^1$ is as defined above, and said N-alkylpyrazole product has Formula (1a):

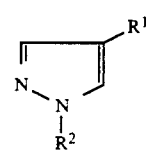

wherein $R^1$ and $R^2$ are are as defined above.

3. The process of claim 1, wherein said aliphatic hydrocarbon is hexane or heptane; the aromatic hydrocarbon is benzene, toluene or xylene; the halogen-substituted aromatic hydrocarbon is chlorobenzene, dichlorobenzene or 3,4-dichlorotoluene; the ether is diethyl ether, di-n-propyl ether, diisopropyl ether, methyl-t-butyl ether, ethylene glycol dibutyl ether, diethylene glycol dibutyl ether, tetrahydrofuran or dioxane; and the aprotic polar solvent is N,N-dimethylformamide or acetonitrile.

4. The process according to claim 1, wherein $R^2$ represents a methyl group.

5. The process according to claim 1, wherein $R^1$ and $R^2$ each represents a methyl group.

6. The process according to claim 1, wherein the alkali metal or the alkali metal containing base is at least one selected from the group consisting of sodium hydride, potassium hydride, lithium hydride, sodium, metal potassium, metal lithium, metal sodium hydroxide, potassium hydroxide, lithium hydroxide, sodium methoxide, sodium ethoxide, potassium methoxide, potassium ethoxide, potassium t-butoxide, butyl lithium and lithium diisopropylamide.

7. The process according to claim 1, wherein sodium metal or potassium metal is reacted in the molten state with N-unsubstituted pyrazoles represented by the formula (2) to form an alkali metal pyrazole salt of.

8. The process according to claim 1, wherein at least one alkali metal-containing base selected from the group consisting of sodium methoxide, sodium ethoxide, potassium methoxide, potassium ethoxide, potassium t-butoxide, sodium hydroxide, potassium hydroxide and lithium hydroxide is reacted with an N-unsubstituted pyrazole represented by the formula (2) while distilling off an alcohol or water to form an alkali metal pyrazole salt.

9. The process according to claim 1, wherein the alkylating agent is at least one member selected from the group consisting of methyl chloride, methyl bromide, methyl iodide, ethyl chloride, ethyl bromide, ethyl iodide, propyl chloride, propyl bromide, propyl iodide, isopropyl chloride, isopropyl bromide, isopropyl iodide, dimethyl sulfate and diethyl sulfate.

10. The process for according to claim 1, wherein the reaction temperature is from $-10°$ to $200°$ C.

* * * * *

UNITED STATES PATENT AND TRADEMARK OFFICE
CERTIFICATE OF CORRECTION

PATENT NO. : 5,153,329
DATED : October 6, 1992
INVENTOR(S) : MURAKAMI ET AL It is certified that error appears in the above-identified patent and that said Letters Patent is hereby corrected as shown below:

| COL. | LINE | |
|---|---|---|
| 7, | 67, | Claim 1, delete "N-substituted" and insert --N-unsubstituted--; |
| 8, | 37, | Claim 2, delete "are" (first occurrence); |
| 8, | 64, | Claim 7, delete "of". |

Signed and Sealed this

Twenty-eighth Day of December, 1993

Attest:

BRUCE LEHMAN

*Attesting Officer*    *Commissioner of Patents and Trademarks*